United States Patent [19]

Powell

[11] 4,237,164
[45] Dec. 2, 1980

[54] CYCLOPROPANECARBOXYLATE PESTICIDES

[75] Inventor: James E. Powell, Ripon, Calif.

[73] Assignee: Shell Oil Company, Houston, Tex.

[21] Appl. No.: 39,099

[22] Filed: May 14, 1979

[51] Int. Cl.³ .................... A01N 37/34; A01N 53/00;
C07C 69/743; C07C 121/75
[52] U.S. Cl. .................... 424/304; 260/326 A;
260/347.4; 260/465 D; 260/544 L; 424/274;
424/285; 424/305; 560/124; 562/506
[58] Field of Search ........... 260/465 D, 347.4, 465 D;
560/124; 424/304, 305

[56] References Cited

U.S. PATENT DOCUMENTS

| 3,355,481 | 11/1967 | Olechowski | 560/124 |
| 4,024,163 | 5/1977 | Elliott et al. | 260/347.4 |

*Primary Examiner*—Dolph H. Torrence

[57] ABSTRACT

Compounds of the formula

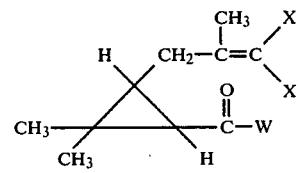

wherein X is halogen, W is a chlorine or bromine atom or —OR in which R is H, a salt-forming cation, an alkyl group or the residue of a pyrethroid alcohol are new pesticides or intermediates therefore. The compounds are prepared using a multi-step synthesis starting from the natural terpene, 3-carene.

5 Claims, No Drawings

CYCLOPROPANECARBOXYLATE PESTICIDES

BACKGROUND OF THE INVENTION

Field of the Invention

The present invention is directed to new cyclopropane compounds, their use in pest control and to pest control formulations containing the new cyclopropanecarboxylates.

SUMMARY OF THE INVENTION

The present invention relates to new cyclopropane compounds of the formula

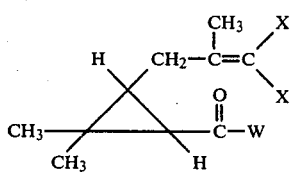

wherein each X is a halogen atom having an atomic number of from 9 to 35, inclusive; W is a chlorine or bromine atom or —OR in which R represents a hydrogen atom, a salt-forming cation, an alkyl group containing from 1 to 20 carbon atoms or a group of the formula

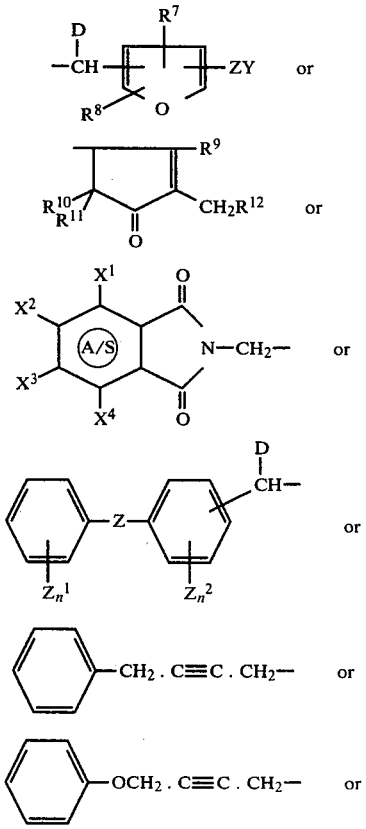

wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represents hydrogen or an alkyl or alkenyl group, $R^9$ represents hydrogen or a methyl group, $R^{10}$ and $R^{11}$ represent hydrogen or an alkyl group, $R^{12}$ represents an organic radical having carbon-carbon unsaturation in a position α to the $CH_2$ group to which $R^{12}$ is attached, A/S indicates an aromatic ring or a dihydro or tetrahydro analog thereof, $X^1$, $X^2$, $X^3$ and $X^4$, which may be the same or different, each represents hydrogen, halogen or a methyl group, $X^5$, which may be the same or different, each represents halogen, D represents H, —CN, —C≡CH or

in which $R^{13}$ and $R^{14}$ may be the same or different, each represents a hydrogen atom or an alkyl group containing from 1 to 10 carbon atoms, Z represents —$CH_2$—, —O—, —CO—, or —S—, $Z^1$ and $Z^2$, which may be the same or different, each represents halogen or an alkyl group containing 1 to 4 carbon atoms and n is 0, 1 or 2, with the proviso that when D is —CN, —C≡CH or

then the alcohol moiety is in the R,S-racemic or in the S-optical configuration.

In the above formulas, suitable halogen substituents are chlorine, fluorine or bromine.

Examples of species within the scope of the present invention include:
α-cyano-3-phenoxybenzyl 2,2-dimethyl-3-(2-methyl-3,3-dibromo-2-propenyl)cyclopropanecarboxylate,
α-cyano-3-phenoxybenzyl 2,2-dimethyl-3-(2-methyl-3,3-difluoro-2-propenyl)cyclopropanecarboxylate,
5-benzyl-3-furylmethyl 2,2-dimethyl-3-(2-methyl-3,3-dichloro-2-propenyl)cyclopropanecarboxylate,
5-benzyl-3-furylmethyl 2,2-dimethyl-3-(2-methyl-3,3-dibromo-2-propenyl)cyclopropanecarboxylate,
5-benzyl-3-furylmethyl 2,2-dimethyl-3-(2-methyl-3,3-difluoro-2-propenyl)cyclopropanecarboxylate,
3-phenoxybenzyl 2,2-dimethyl-3-(2-methyl-3,3-dichloro-2-propenyl)cyclopropanecarboxylate,
α-ethynyl-3-phenoxybenzyl 2,2-dimethyl-3-(2-methyl-3,3-dibromo-2-propenyl)cyclopropanecarboxylate,
α-thiocarbamoyl-3-phenoxybenzyl 2,2-dimethyl-3-(2-methyl-3,3-difluoro-2-propenyl)cyclopropanecarboxylate,
3-phenylthiobenzyl 2,2-dimethyl-3-(2-methyl-3,3-dibromo-2-propenyl)cyclopropanecarboxylate, 3,4,5,6-tetrahydrophthalimidomethyl 2,2-dimethyl-3-(2-methyl-3,3-dichloro-2-propenyl)cyclopropanecarboxylate.

The cyclopropane compounds exhibit geometrical and optical isomerism by virtue of the double bond and the two asymmetric centers in the cyclopropane ring. Consequently, the compounds can be prepared in optically active forms, which can subsequently be mixed together, or as racemic mixtures, which can subsequently be prepared as optically active forms. Because they usually provide the highest degree of pest control, the (1R,cis) esters are preferred although the (1R,trans) esters are also active. In the esters of α-substituted alcohols in which D in formulas I or IV is other than hydrogen, there is a further possibility of optical isomerism, i.e., as R or as S optical configuration. The cyano esters in which these alcohols exist in the R optical configuration are without practical pest control activity. In addition, optically active forms can be separated into the individual geometrical isomers.

Matsui et al., *Agr. Biol. Chem.*, 29, No. 8, p. 784–6, (1965) discloses the preparation of 2,2-dimethyl-3-(2-oxopropyl)cyclopropanecarboxylic acid of formula VIII

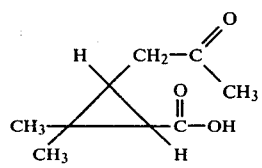

VIII from $\Delta^3$-carene.

This acid was converted into the corresponding methyl ester by treatment with ethereal diazomethane, for example similar to the preparation of the methyl ester as described in Matsui et al. Treatment of the methyl ester with a carbon tetrahalide and a phosphorous triamide afforded methyl 2,2-dimethyl-3-(2-methyl-3,3-dihalo-2-propenyl)cyclopropanecarboxylate. Hydrolysis of this ester under basic conditions, for example with a 10% sodium hydroxide solution, yielded the 2,2-dimethyl-3-(2-methyl-3,3-dihalo-2-propenyl)cyclopropanecarboxylic acid of formula IX.

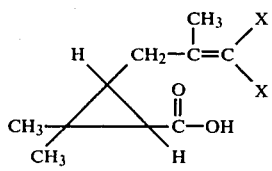

IX

The alcohols of the groups of formulas I through VII, inclusive, are known in the art, as for example in Elliott et al., U.S. Pat. Nos. 3,567,740 and 3,922,269 or Belgian Pat. No. 839,360 and 862,109. The pest control esters of the present invention can be prepared by esterification involving the reaction of an alcohol or derivative thereof of formula RQ, e.g., of formula X, and a cyclopropanecarboxylic acid or derivative of formula XI

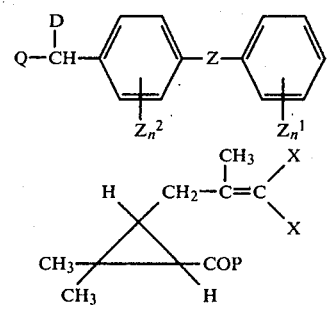

wherein Q and COP are functional groups or atoms which will react to form an ester linkage and D, Z, $Z^1$ and $Z^2$ are as defined above.

It is usually convenient in practice either to treat the acid or acid halide with the alcohol (COP=COOH or CO-halide and Q=OH) or to treat a halogeno compound (Q=halogen) with a salt of the carboxylic acid (COP=COO—M) where M is, for example, a silver or ammonium cation.

It can be useful to prepare the intermediate alkyl ester as tert-butyl ester (R=tert-butyl), which can be selectively converted under acid conditions to give the free acid which can be esterified, e.g., after conversion to the acid halide, to a pesticidal ester.

Suitable routes to the esters in which D is

are similar to those described in Belgian Pat. No. 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent, such as dimethylformamide or hexamethylphosphoramide. The catalyst is preferably a strong nitrogeneous base, particularly a tertiary amine such as triethylamine, trimethylamine, or the like, or an alkanolamine, such as triethanolamine, and the like. The reaction can be carried out at room temperature. It is desirable that the reaction solution be saturated with hydrogen sulfide.

Alcohols of formula RQ where R is a group of formula IV may be prepared by reduction of the corresponding acids, esters or aldehydes, e.g., with hydride, or by conversion of the corresponding halide to an ester, e.g., by reaction with sodium acetate, followed by hydrolysis of the ester, or by reaction with formaldehyde or a Grignard reagent derived from the corresponding halide. The halides of formula RQ where R is a group of formula IV can be prepared by halomethylation of the compound

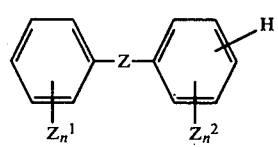

or side chain halogenation of

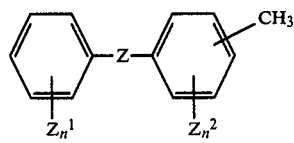

As stated earlier, the esters wherein W is OR in which R is a group of formula I–VII are useful pest control agents having the ability to knock down insects, such as houseflies, or repel mites and/or to kill insects or mites. The particular mode of pest control activity (high knockdown, repelling or killing action) can vary with the individual cyclopropanecarboxylate ester of the invention and thus depends on the specific combination of acid and alcohol moieties.

The invention includes, within its scope, pest control compositions comprising an agriculturally acceptable adjuvant—that is, at least one carrier or a surface-active-agent—and, as active ingredient, at least one pest control ester of this invention. Likewise, the invention includes also a method of controlling insect, acarine or other arthropod pests at a locus which comprises applying to the pests or to the locus a pest controlling effective amount of at least one ester of the invention.

With respect to the spectrum of pesticidal activity, the compounds of this invention exhibit a selective or non-selective activity as insecticides or acaricides against one or more species of such orders as Coleoptera, Lepidoptera (especially larvae), Diptera, Orthoptera, Hemiptera, Homoptera and Acarina depending upon the specific combination of acid and alcohol moieties according to the present invention. The compositions according to the present invention are useful for controlling one or more disease-carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamond-back moths (*Plutella maculipennis* Curtis), imported cabbage worm (*Pieris rapae* Linne), rice stem borers (*Chilo Suppressalis* Walker), corn earworm larvae (*Heliothis zea* Boddie), aphids, tortrixes, leaf-miners and the like.

The pesticidal esters of the invention are used for harvested crops, horticultural application, forests, cultures in green house, and packaging materials for foodstuffs, household applications and as ectoparasicticides.

The term "carrier" as used herein means a material that may be inorgaic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di-, and trialkylamines; condensates of these with ethylene oxide and-/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75 %w of toxicant and usually contain, in addition to solid carrier, 3–10 %w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10 %w of toxicant. Granules may be manufactured by extrusion of plastics, agglomeration or impregnation techniques. Generally, granules will contain ½–25 %w toxicant and 0–10 %w of additives such as stabilizers, slow release modifiers and binding agents. Emulsifiable concentrates usually contain, in addition to the solvent, and when necessary, cosolvent, 10–50 %w/v toxicant, 2–20 %w/v emulsifiers and 0–20 %w/v of appropriate additives such as stabilizers, penetrants and corrosion inhibitors. Suspension concentrates are compounded so as to obtain a stable, nonsedimenting, flowable product and usually contain 10–75 %w toxicant, 0–5 %w of dispersing agents, 0.1–10 %w of suspending agents such as protective colloids and thixotropic agents, 0–10 %w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboxamide, octachlorodipropyl ether, isobornyl thiocyanoacetate, and other synergists used for allethrin and pyrethrin. Useful compositions can be prepared with other biological chemicals including other cyclopropanecarboxylates, organic phosphate-type insecticides and carbamate-type insecticides.

The compositions of the invention are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of active ingredient of this invention at the locus to be protected—i.e., the applied dosage—is of the order of 0.01% to 0.5% based on the total weight of the formulation, though under some circumstances the effective concentration will be as little as 0.001% or as much as 2%, on the same basis.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

Methyl (1R,cis)-2,2-dimethyl-3-(2-oxopropyl)cyclopropanecarboxylate

To a solution of 5.0 g of potassium hydroxide in 8 ml water, 25 ml of ethanol was added and heated to 82° C. To this alkali solution 21.5 g of N-methyl-N-nitroso-p-toluenesulfonamide in 200 ml diethyl ether was added dropwise while the temperature slowly dropped to 70° C. and an ethereal solution of diazomethane was allowed to distil. An additional 40 ml of diethyl ether was added and allowed to distil. To the distillate was added dropwise at 0° C. 11.3 g of (1R,cis)-2,2-dimethyl-3-(-2-oxopropyl)cyclopropanecarboxylic acid in (15 ml) diethyl ether. The solution was allowed to warm to room temperature, stirred for 1 hour, washed with 200 ml saturated sodium bicarbonate solution and then with 200 ml saturated sodium chloride solution, dried over magnesium sulfate and stripped to yield 12.5 g of amber oil. The product was distilled through a Kugelrohr apparatus at 55° C. at 0.06 mm Hg.

EMBODIMENT 2

Methyl (1R,cis)-2,2-dimethyl-3-(2-methyl-3,3-dichloro-2-propenyl)cyclopropanecarboxylate To a solution of 10.16 g carbon tetrachloride in 150 ml of pentane held at 0° C. under nitrogen, 10.76 g of hexamethyl phosphorous triamide was added by syringe. After the mixture was stirred for 15 minutes, 5.70 g of the product of Embodiment 1 above was added by syringe. The resulting mixture was stirred in the cold for 3 hours, and then at room temperature for an additional 2 hours, diluted with pentane, washed twice with 200 ml of water and then with 200 ml of saturated sodium chloride solution, dried over magnesium sulfate, and stripped to give 6.3 g of a yellow oil. This oil was added to a mixture of 10.2 g of hexamethyl phosphorous triamide and 10.16 g carbon tetrachloride in pentane at 0° C. and stirred for 1 hour. The resulting mixture was diluted with 100 ml pentane, washed twice with 200 ml water and then with 200 ml saturated sodium chloride, dried over magnesium sulfate and stripped to yield 6.0 g of product as an amber oil which distilled at 78°–83° C. at 0.04 mm Hg.

EMBODIMENT 3

(1R,cis)-2,2-Dimethyl-3-(2-methyl-3,3-dichloro-2-propenyl)cyclopropanecarboxylic acid To a partial solution of the product of Embodiment 2 above in 50 ml methanol was added 10 ml of 10% sodium hydroxide solution. The reaction mixture was refluxed for about 12 hours, cooled to room temperature, diluted with 50 ml of water and cooled to 5°–10° C. The aqueous solution was acidified to a pH of 1 with 2N hydrochloric acid, extracted twice with 200 ml methylene chloride, dried over magnesium sulfate and stripped to yield 4.4 g of amber oil which crystallized upon cooling. 4.2 g of this material was dissolved in 8 ml of methanol and mixed with 80 ml of 10% sodium hydroxide. After stirring for 5 minutes, the mixture was extracted twice with 200 ml of methylene chloride. The resulting aqueous phase was chilled, acidified with 2N hydrochloric acid, and extracted twice with 200 ml methylene chloride. The extract was dried over magnesium sulfate and stripped to give 3.0 g of light amber oil. The oil was crystallized from pentane to yield 1.5 g of product as a white solid; m.p. 58.5°–60.0° C.

EMBODIMENT 4

α-Cyano-3-phenoxybenzyl (1R,cis)-2,2-dimethyl-3-(2-methyl-3,3-dichloro-2-propenyl)cyclopropanecarboxylate To a solution of 0.99 g potassium carbonate, 0.1 g tetrabutylammonium sulfate and 0.1 g benzyltriethylammonium chloride in 12 ml of water, 3.4 g of the acid of Embodiment 3 above in 20 ml of toluene was added. The reaction mixture was stirred rapidly with the addition of 4.13 g of α-cyano-3-phenoxybenzyl bromide. The resulting mixture was heated to 65° C. and stirred for 6 hours. The toluene phase was separated, washed successively with water, saturated sodium bicarbonate solution, and saturated sodium chloride solution, dried over magnesium sulfate and stripped to yield an amber oil. The oil was chromatographed on silica gel using ether:hexane (1:12) as the eluent. The fourth fraction was stripped under high vacuum for 24 hours to give the desired product; $[\alpha]_D^{25} = -0.11$ (CHCl$_3$; C=2 g/100 ml).

I claim:

1. A (1R,cis) compound of the formula

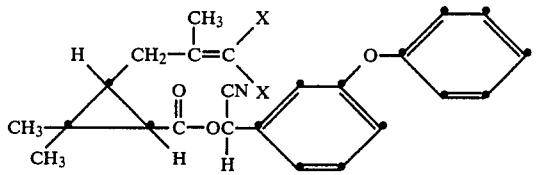

wherein X is chlorine or bromine, with the priviso that the alcohol moiety is in the R,S-racemic or the S-optical configuration.

2. A compound according to claim 1 wherein each X is chlorine.

3. A compound according to claim 1 wherein each X is bromine.

4. A pest control composition comprises a pest controlling effective amount of compound according to claim 1, and at least one agriculturally acceptable surface-active agent or carrier therefore.

5. A method of controlling pests which comprises applying to the pests or their habitat a pest controlling effective amount of a compound according to claim 1.

* * * * *